United States Patent
Srivastava et al.

(10) Patent No.: US 9,610,010 B2
(45) Date of Patent: Apr. 4, 2017

(54) SYSTEMS AND METHODS FOR ANALYSIS OF OCULAR INFLAMMATION

(71) Applicant: THE CLEVELAND CLINIC FOUNDATION, Cleveland, OH (US)

(72) Inventors: Sunil K. Srivastava, Shaker Hts., OH (US); Sumit Sharma, Durham, NC (US); Careen Y. Lowder, Orange Village, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 14/844,137

(22) Filed: Sep. 3, 2015

(65) Prior Publication Data
US 2016/0058280 A1    Mar. 3, 2016

Related U.S. Application Data

(60) Provisional application No. 62/045,079, filed on Sep. 3, 2014.

(51) Int. Cl.
| | |
|---|---|
| *A61B 3/14* | (2006.01) |
| *A61B 3/00* | (2006.01) |
| *A61B 3/10* | (2006.01) |
| *G06F 19/00* | (2011.01) |

(52) U.S. Cl.
CPC ............ *A61B 3/0025* (2013.01); *A61B 3/102* (2013.01); *A61B 3/14* (2013.01); *G06F 19/3431* (2013.01)

(58) Field of Classification Search
USPC .................................................. 351/200–246
See application file for complete search history.

(56) References Cited

U.S. PATENT DOCUMENTS

| | | | |
|---|---|---|---|
| 8,632,180 B2 | 1/2014 | Narasimha-Iyer | |
| 2003/0216621 A1* | 11/2003 | Alpert .................. | A61B 5/0215 600/300 |
| 2011/0299034 A1* | 12/2011 | Walsh .................... | A61B 3/102 351/206 |
| 2012/0020539 A1 | 1/2012 | Derr et al. | |

OTHER PUBLICATIONS

Agarwal et al. "High-speed optical coherence tomography for imaging anterior chamber inflammatory reaction in uveitis: clinical correlation and grading." American journal of ophthalmology 147.3 (2009): 413-416.

(Continued)

*Primary Examiner* — Mohammed Hasan
(74) *Attorney, Agent, or Firm* — Tarolli, Sundheim, Covell & Tummino LLP

(57) ABSTRACT

One aspect of the present disclosure relates to a system that can perform an automated analysis of ocular inflammation (e.g., based on a non-contact image of the eye), which can lead to determining score for the ocular inflammation. The system can include a memory to store computer-executable instructions; and a processor that executes the computer-executable instructions to at least: receive an image of a portion of an eye taken by a non-contact imaging modality; determine a diagnostic parameter for ocular inflammation from the image of the portion of the eye; score the ocular inflammation with a continuous value based on the diagnostic parameter; and output the score to a display device.

16 Claims, 6 Drawing Sheets

(56) References Cited

OTHER PUBLICATIONS

Lowder, et al. "Anterior Chamber Cell Grading with High-Speed Optical Coherence Tomography." Investigative Ophthalmology & Visual Science 45.13 (2004): 3372-3372.
Li et al. "Anterior Chamber Cell Grading by Optical Coherence TomographyAnterior Chamber Cell Grading by OCT." Investigative ophthalmology & visual science 54.1 (2013): 258-265.

* cited by examiner

SYSTEMS AND METHODS FOR ANALYSIS OF OCULAR INFLAMMATION

CROSS-REFERENCE TO RELATED APPLICATIONS

This application claims the benefit of U.S. Provisional Patent Application No. 62/045,079, filed Sep. 3, 2014, entitled, "SYSTEMS AND METHODS FOR ANALYSIS OF OCULAR INFLAMMATION". The subject matter of this provisional application is incorporated herein by reference in its entirety.

TECHNICAL FIELD

The present disclosure generally relates to analysis of ocular inflammation and, more particularly, to systems and methods that can analyze ocular inflammation in an automated manner.

BACKGROUND

Ocular inflammation generally relates to inflammation of any part of the eye, including both intraocular inflammation and inflammation of the sclera. Intraocular inflammation can be further divided into inflammation of the anterior segment (located between the iris and the cornea) and inflammation of the posterior segment (vitreous cavity). Each type of ocular inflammation can exhibit a different form of inflammation that can be measured in different ways.

Clinicians can diagnose ocular inflammation based on a clinical exam that employs a diagnostic device, such as a slit lamp microscope or an indirect ophthalmoscope. Based on the clinical examination, the clinician can grade the extent of the ocular examination based on a standard, categorical scale. The standard, categorical scale is designed to allow for comparison in both clinical practice and clinical trials; however, the rankings suffer from variability between clinicians and even between patients with the same clinician. Moreover, although each type of ocular inflammation can exhibit different forms of inflammation, the extents of the different types of ocular inflammation can be graded according to the same standardized, categorical scale with a finite number of grades, such as the six-grade scale (providing rankings of 0, trace, 1+, 2+, 3+ and 4+) provided by the Standardization of Uveitis Nomenclature (SUN) Working Group. However, since the scale includes a finite number of grades, there is an inability to discern small changes in inflammation grades, which could be clinically significant.

SUMMARY

The present disclosure generally relates to analysis of ocular inflammation and, more particularly, to systems and methods that can analyze ocular inflammation in an automated manner. In other words, a diagnostic parameter can be identified and scored in an automated fashion, with little to no direct human control, to illustrate small changes in the inflammation, which can be clinically important. In some instances, the diagnostic parameter can be identified in a non-contact (e.g., optical coherence tomography (OCT)) image of the eye.

In one aspect, the present disclosure can include a system that analyzes ocular inflammation. The system can include a memory to store computer-executable instructions and a processor that executes the computer-executable instructions. Upon execution of the instructions, an image of a portion of an eye taken by a non-contact imaging modality can be received. A diagnostic parameter for ocular inflammation can be determined from the image of the portion of the eye. The ocular inflammation can be scored with a continuous value based on the diagnostic parameter; and the score can be output to a display device.

In another aspect, the present disclosure can include a method for analyzing ocular inflammation. One or more acts of the method can be represented by computer-executable instructions that can be executed by a system comprising a processor. An optical coherence tomography image of at least a portion of an eye is received. Based on the optical coherence tomography image, a diagnostic parameter for ocular inflammation is determined. The ocular inflammation is scored with a continuous value based on the diagnostic parameter and the score is output to a display device.

In a further aspect, the present disclosure can include a non-transitory computer-readable medium storing instructions executable by one or more processors to cause a computing device to perform operations. The operations can include: receiving an optical coherence tomography image of a cross section of a patient's eye; identifying inflammatory cells in the cross-section of the patient's eye based on the optical coherence tomography image; counting the identified inflammatory cells; scoring a degree of ocular inflammation for the patient based on the counting relative to a previously determined score for the patient; and outputting the score to a display device.

BRIEF DESCRIPTION

The foregoing and other features of the present invention will become apparent to those skilled in the art to which the present invention relates upon reading the following description with reference to the accompanying drawings, in which.

DETAILED DESCRIPTION

I. Definitions

Figure 1:
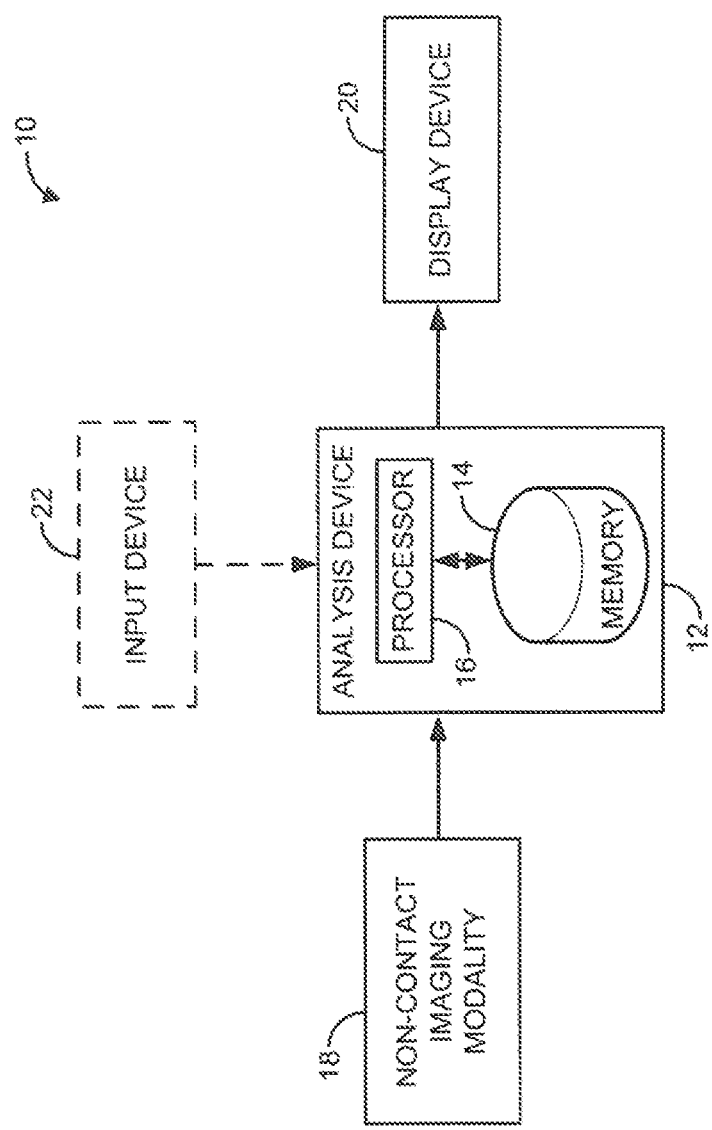
FIG. 1 is a block diagram showing a system that analyzes ocular inflammation in accordance with an aspect of the present disclosure.

In the context of the present disclosure, the singular forms "a," "an" and "the" can also include the plural forms, unless the context clearly indicates otherwise.

The terms "comprises" and/or "comprising," as used herein, can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

Additionally, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or acts/steps) is not limited to the order presented in the claims or figures unless specifically indicated otherwise.

As used herein, the term "non-contact imaging modality" can refer to an imaging modality that can obtain an image of a target area through a transparent window or membrane. In some instances, a non-contact imaging modality can be a non-invasive imaging modality. One example of a non-contact imaging modality is optical coherence tomography (OCT).

As used herein, the term "target area" can correspond to at least a portion of a patient's eye. For example, the target area can include of the sclera of the eye, the posterior segment of the eye, and/or the anterior chamber of the eye, As used herein, the term "ocular inflammation" can refer to inflammation of any part of the eye, including both intraocular inflammation (e.g., inflammation of the anterior segment (located between the iris and the cornea), inflammation of the posterior segment (vitreous cavity), and/or inflammation of the sclera. In other instances, ocular inflammation can refer to inflammation of the retina.

As used herein the term "diagnostic parameter" can refer to a parameter that can be identified from an image from a non-contact imaging modality that can facilitate the diagnosis of ocular inflammation. For example, the diagnostic parameter can be a number of inflammatory cells, a thickness of the sclera, a density of the sclera, a density of opacity or haze, and/or an amount of leakage from the retina. In some instances, the diagnostic parameter can be identified with and/or correlated to a score.

As used herein, the term "score" can refer to an indication of ocular inflammation based on the diagnostic parameter. The score can be used to discern small changes in inflammation grades, which could be clinically significant. In some instances, the score can be based on a continuous measurement scale.

As used herein, the term "continuous measurement scale" can refer to a type of measurement scale that can illustrate small changes in the diagnostic parameter. In other words, the continuous measurement scale is not a categorical scale that is categorized with a finite number of grades (e.g., 6 grades). The continuous measurement scale has a theoretically infinite number of possible values.

As used herein, the term "subject" can refer to any warm-blooded organism including, but not limited to, a human being, a pig, a rat, a mouse, a dog, a cat, a goat, a sheep, a horse, a monkey, an ape, a rabbit, a cow, etc. The terms "subject" and "patient" can be used interchangeably herein.

As used herein, the term "automated" can refer to a process that operates by itself with little to no direct human control. In some instances, an automatic process can operate with no direct human control other than an initial input (e.g., a non-contact image). In other instances, the automated process can operate with user-defined parameters (e.g., setting a threshold reflectance, so that one or more pixels exhibiting a reflectance greater than the threshold can be identified as inflammatory cells).

II. Overview

The present disclosure generally relates to analysis of ocular inflammation and, more particularly, to systems and methods that can analyze ocular inflammation in an automated manner. The analysis can include identifying and scoring a diagnostic parameter of inflammation in a manner that is not hampered by an intra-interpreter bias. Advantageously, the automated analysis can determine a score that can illustrate small, often clinically important, changes in the inflammation, which may be missed with traditional scoring methods. Such automated scoring can allow clinicians to assess these important small changes in the inflammation.

III. Systems

One aspect of the present disclosure, illustrated in FIG. 1, can include a system 10 that can analyze ocular inflammation in an automated manner. The system 10 can include an analysis device 12 that can automatically identify a diagnostic parameter in a non-contact image of at least a portion of a patient's eye and score the diagnostic parameter according to a continuous measurement scale. Advantageously, the continuous measurement scale can enable users to see small changes in the inflammation, which are often clinically important, but can be missed by traditional scores based on a categorical measuring scale. Through the continuous measurement scale, the system 10 can allow clinicians to assess such clinically important small changes in the inflammation.

The system 10 can include a non-contact imaging modality 18 that can provide an input to the analysis device 12. The input can be related to the non-contact image of the person's eye. For example, the input can include one or more non-contact images and/or data representing the one or more non-contact images. As another example, the input can be a video taken by the non-contact imaging modality 18 or data representing one or more video frames taken by the non-contact imaging modality 18. In some instances, the non-contact imaging modality 18 can be optical coherence tomography (OCT). One example of OCT is spectral domain optical coherence tomography (SDOCT). In other instances, the non-contact imaging modality 18 can be an OCT-based angiography device.

The system 10 can also include a display device 20 that can receive and display an output from the analysis device 12. The display device 20 can provide a mechanism for a user to receive and interpret the score. In some instances, the display device 20 can include a visual and/or graphical display. In other instances, the display device 20 can include an audio display. In some instances, the system 10 can also include an input device 22 that can receive an input from a user changing or providing at least one parameter used by the analysis device 12 in identifying the diagnostic parameter.

The input device 22 and the display device 20 are each communicatively coupled to the analysis device 12 (e.g., via I/O circuitry). In some examples, the display device 20 and the input device 22 can be part of the same device (e.g., a touch screen device). Although the input device 22 and the display device 20 are illustrated as separate from the analysis device 12, one or both of the input device 22 and the display device 20 can be included within the analysis device 12. For example, the display device 20 can be an input device, an output device, and/or an input/output device that can allow a user input and/or a visualization.

Figure 2:
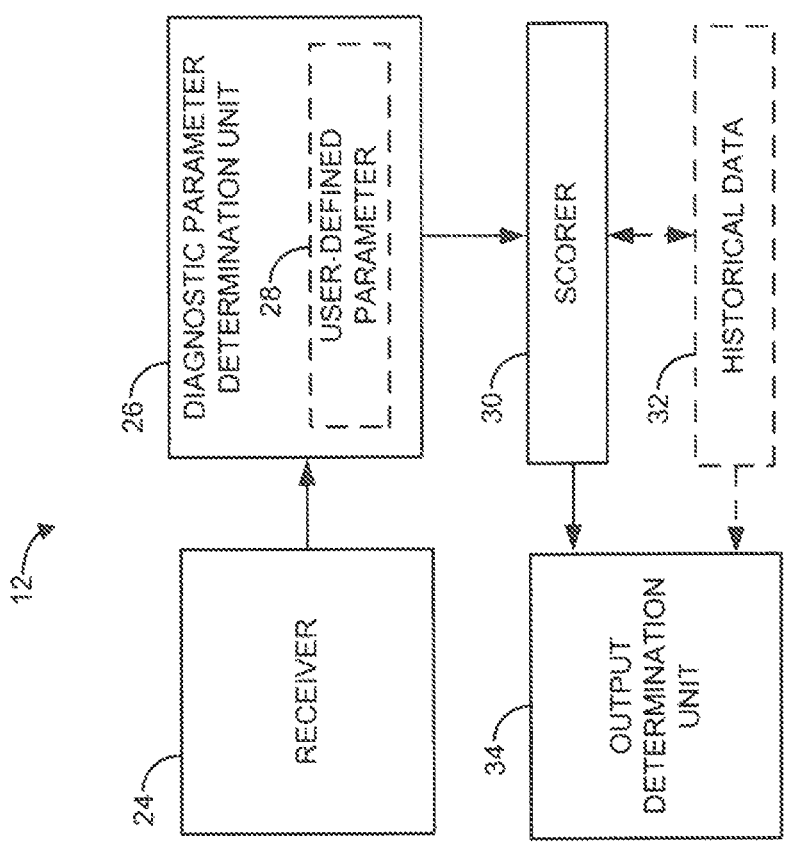
FIG. 2 is a block diagram showing example components of the analysis device of FIG. 1.

The analysis device 12 can be a computing device that can include a non-transitory memory 14 and a processor 16. The non-transitory memory can store computer-executable instructions that are executable by the processor to perform operations leading to the identification and scoring of the diagnostic parameter. FIG. 2 is an illustration of components of the analysis device of FIG. 1 that can occur upon execution of the instructions stored in the non-transitory memory 14.

FIG. 2 is schematically illustrated as a block diagram with the different blocks representing different components. The components can include at least a receiver 24, a diagnostic parameter determination unit 26, a scorer 30, and an output determination unit 34. In some instances, the components can include one or more components that can access or process historical data 32. As described above, the functions of one or more of the components can be implemented by computer program instructions that can be stored in the memory and executed by the processor.

The receiver 24 can be configured to receive an image of at least a portion of a patient's eye taken by a non-contact imaging modality 18 of FIG. 1. The image can be conveyed as a signal that includes data representing the image of the at least the portion of the patient's eye. For example, the image can correspond to a cross section of the eye. The cross section of the eye can correspond to a three-dimensional volume of the portion of the patient's eye (e.g., a three-dimensional cube scan). In some instances, the receiver 24 can perform preprocessing before sending data representing at least a portion of the image to the diagnostic parameter determination unit 26.

The diagnostic parameter determination unit 26 can be configured to determine (and/or identify) a diagnostic parameter for ocular inflammation based on the data representing the image of the eye received from the receiver 24. The ocular inflammation can be inflammation of any part of the eye visible in the image. For example, the ocular inflammation can be intraocular inflammation (e.g., inflammation of the anterior segment (located between the iris and the cornea) and/or inflammation of the posterior segment (vitreous cavity)) and/or inflammation of the sclera. The diagnostic parameter for inflammation of the anterior segment can include the presence of one or more inflammatory cells within the image. The diagnostic parameter for inflammation of the posterior segment can include a density of opacity and/or haze. The diagnostic parameter for inflammation of the sclera can include a thickness of the sclera and/or a density of the sclera. In another example, the ocular inflammation can be inflammation of the retina and the associated diagnostic parameter can be an amount of leakage from the retina.

The diagnostic parameter determination unit 26 can employ an automatic process to identify the diagnostic parameter within the image. The diagnostic parameter can be, for example, cell size, cell pixel intensity, number of cells, or the like, which can be automatically detected in the image and subsequently quantified. In some instances, if the ocular inflammation relates to inflammation of the anterior segment, the diagnostic parameter can correspond to a number of inflammatory cells in the image or a portion of the image. The diagnostic parameter determination unit 26 can identify and count the number of inflammatory cells within the image. In some instances, the identification can be based on a threshold established as to a pixel size and/or a pixel reflectivity within the image compared to a background pixel size and/or a background pixel reflectivity. The threshold can be, for example, twice the pixel reflectivity. However, the threshold can be any user defined value (user-defined parameter 28) that can be input by the input device 22 of FIG. 1. However, the diagnostic parameter can be quantified beyond the threshold. Upon identification, the diagnostic parameter can be sent by the diagnostic parameter determination unit 26 to the scorer 30.

The scorer 30 can be configured to assign a score to the ocular inflammation based on the diagnostic parameter. The score can be a continuous value related to a degree of inflammation. The score can be the diagnostic parameter or a function of the diagnostic parameter. For example, in the case of inflammation of the anterior segment, the score can be based on an absolute number of inflammatory cells in the image. In an example where the image is a three dimensional image, the score for inflammation of the anterior segment can be a volumetric number of inflammatory cells (e.g., the number of cells divided by the volume shown in the image).

In some instances, the score and/or the diagnostic parameter can be stored in memory (e.g., non-transitory memory 14 of FIG. 1) and later used as a reference value. These reference values can be stored as historical data 32 (which includes data recorded at previous times). The historical data 32 can include one or more previous scores and/or diagnostic parameters for a certain patient and/or a population of patients. The historical data 32 can provide a record of ocular inflammation that shows changing and/or consistent scores. In some instances, the scorer 30 can access at least a portion of the historical data 32 and compare the historical data 32 to the identified diagnostic parameter to determine the score.

The scorer 30 can output the score to the output determination unit 34, which can output the score to the display device 20 of FIG. 1. In some instances, the output determination unit 34 can provide data in addition to the score to the display device 20 of FIG. 1. For example, the additional data can include the diagnostic parameter. In other instances, the output determination unit 34 can access the historical data 32 and output a portion of the historical data 32 (e.g., one or more previous scores for the patient) with the current score to provide a comparison between at least two scores to show a relative change in the inflammation and/or the degree of inflammation. The output determination unit 34 can signal the display device 20 of FIG. 1 to generate an alert when the score or a difference between scores is above a threshold, which can be used defined by the input device 22 or can be preset (e.g., a chance of greater than or less than 5% triggers an alarm). The alarm can be an audio alarm, a visual alarm (e.g., flashing on a screen or another graphical feature designed to alert a doctor or other medical professional of the change).

IV. Methods

Figure 3:
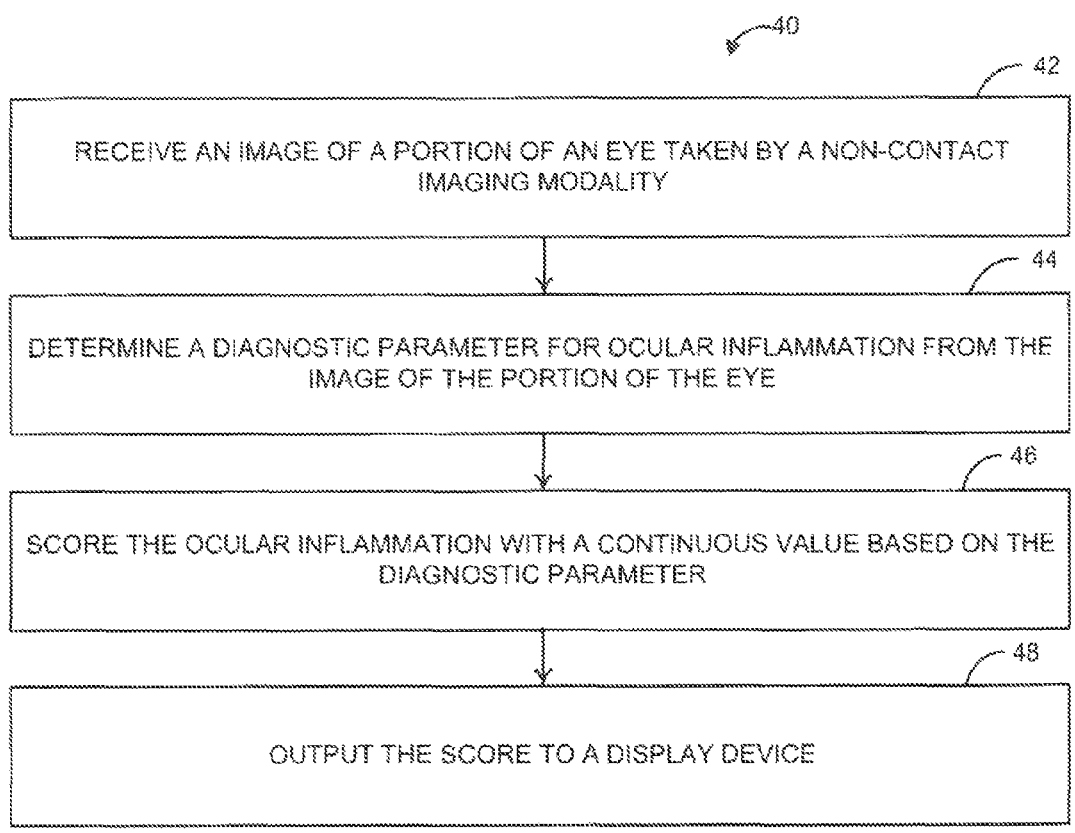
FIG. 3 is a process flow diagram illustrating a method for analyzing ocular inflammation in accordance with another aspect of the present disclosure.
Figure 4:
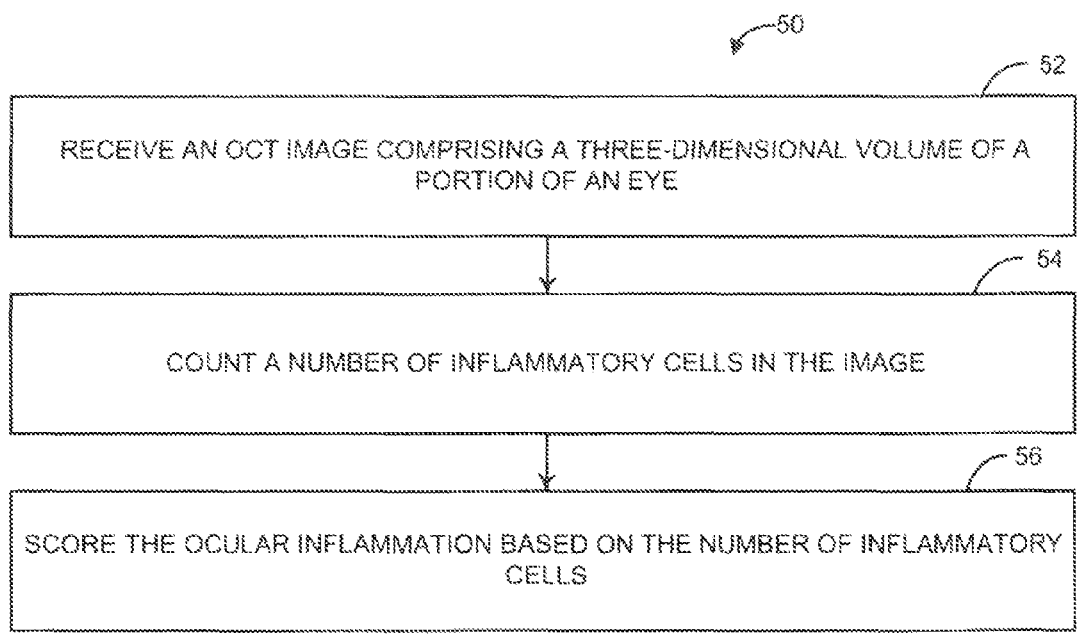
FIG. 4 is a process flow diagram illustrating a method for analyzing ocular inflammation using an optical coherence tomography (OCT) image comprising a three-dimensional volume of a portion of an eye in accordance with another aspect of the present disclosure.

Another aspect of the present disclosure can include methods that can identify and score a diagnostic parameter of inflammation of the eye (e.g., in a non-contact image, such as an optical coherence tomography (OCT) image, of the eye or an angiography study of the eye. The methods can identify and score the diagnostic parameter automatically based on a continuous measurement scale. Advantageously, the continuous measurement scale can allow the score to illustrate small changes in the inflammation, which can be missed by traditional scores based on a categorical measuring scale. An example of a method 40 that can analyze ocular inflammation is shown in FIG. 3. An example of a method 50 for analyzing ocular inflammation using an OCT image comprising a three-dimensional volume of a portion of an eye is shown in FIG. 4. An example of a method 60 for tracking the progress of an optical condition is shown in FIG. 5.

Figure 5:
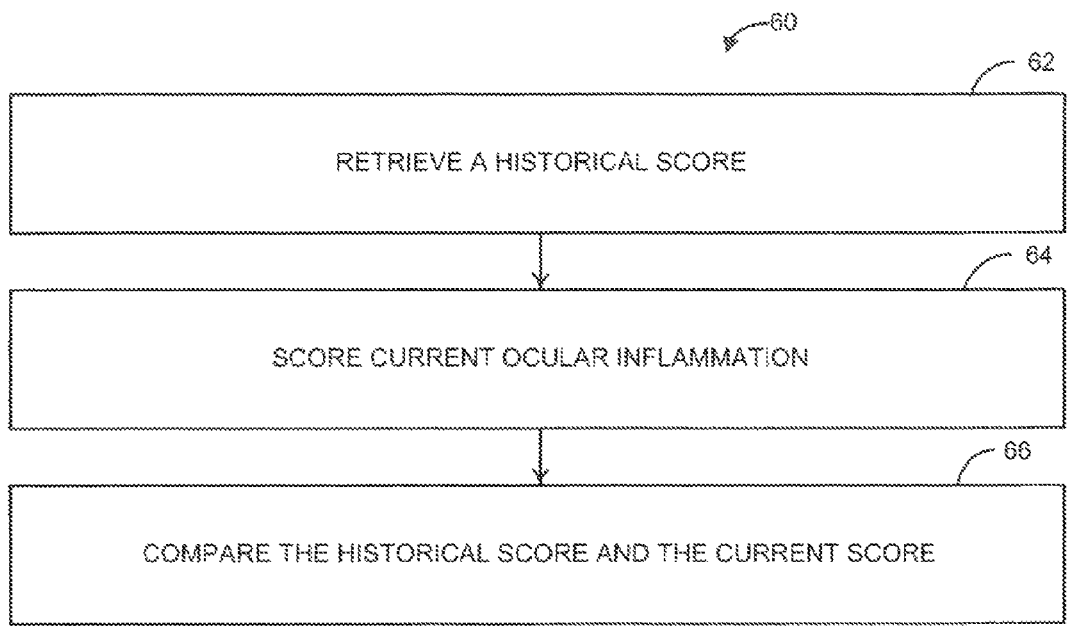
FIG. 5 is a process flow diagram illustrating a method for tracking the progress of an optical condition.

The methods 40, 50, and 60 of FIGS. 3, 4, and 5 are illustrated as process flow diagrams with flowchart illustrations. For purposes of simplicity, the methods 40, 50, and 60 are shown and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the methods 40, 50, and 60.

One or more blocks of the respective flowchart illustrations, and combinations of blocks in the block flowchart illustrations, can be implemented by computer program instructions. These computer program instructions can be stored in memory and provided to a processor of a general purpose computer, special purpose computer, and/or other programmable data processing apparatus to produce a machine, such that the instructions, which execute via the processor of the computer and/or other programmable data processing apparatus, create mechanisms for implementing the steps/acts specified in the flowchart blocks and/or the associated description. In other words, the steps/acts can be implemented by a system comprising a processor that can access the computer-executable instructions that are stored in a non-transitory memory.

The methods 40, 50, and 60 of the present disclosure may be embodied in hardware and/or in software (including firmware, resident software, micro-code, etc.). Furthermore, aspects of the present disclosure may take the form of a computer program product on a computer-usable or computer-readable storage medium having computer-usable or computer-readable program code embodied in the medium for use by or in connection with an instruction execution system. A computer-usable or computer-readable medium may be any non-transitory medium that can contain or store the program for use by or in connection with the instruction or execution of a system, apparatus, or device Referring to FIG. 3, an aspect of the present disclosure can include a method 40 for analyzing ocular inflammation. In some instances, the method 40 can be performed by components of an analysis device 12. According to method 40, a diagnostic parameter for inflammation can be automatically identified within a non-contact image. The identified diagnostic parameter can be scored according to a continuous measurement scale. The continuous measurement scale can enable users to see small changes in the inflammation, which can be missed by traditional scores based on a categorical measuring scale. In some instances, these small changes can be clinically important. Scoring the inflammation according to the continuous measurement scale can allow clinicians to assess such clinically important small changes in the inflammation.

At 42, an image of a portion of an eye taken by a non-contact imaging modality (e.g., non-contact imaging modality 18) can be received. The image can be conveyed in a signal that includes data representing at least a portion of the non-contact image. In some instances, the non-contact image can be an OCT image. For example, the image can correspond to a cross section of the eye. The cross section of the eye can correspond to a three-dimensional volume of the eye (e.g., a three-dimensional cube scan).

At 44, a diagnostic parameter for ocular inflammation can be determined (and/or identified) based on the non-contact image. The determination can be an automatic process. The ocular inflammation can be inflammation of any part of the eye visible in the image. For example, the ocular inflammation can be intraocular inflammation (e.g., inflammation of the anterior segment (located between the iris and the cornea) and/or inflammation of the posterior segment (vitrious cavity)) and/or inflammation of the sclera. The diagnostic parameter for inflammation of the anterior segment can include the presence of one or more inflammatory cells within the image. The diagnostic parameter for inflammation of the posterior segment can include a density of opacity and/or haze. The diagnostic parameter for inflammation of the sclera can include a thickness of the sclera and/or a density of the sclera. In cases where the image is a three-dimensional volume image, the diagnostic parameter can be a volumetric parameter.

At 46, the ocular inflammation can be scored based on the diagnostic parameter. In some instances, the score can be a continuous value related to a degree of inflammation. The scoring can be an automatic process in which the score can be based on a continuous measurement scale. For example, in the case of inflammation of the anterior segment, a number (e.g., an absolute number and/or a volumetric number) of inflammatory cells can be determined (e.g., counted). The number of inflammatory cells can be scored and the score can be output. In some instances, the score can indicate the number of inflammatory cells and/or a function of the number of inflammatory cells. At 48, the score can be output to a display device.

FIG. 4 illustrates a method 50 for analyzing inflammation in a three-dimensional OCT image. At 52, an OCT image comprising a three-dimensional volume of a portion of an eye can be received. At 54, a number of inflammatory cells can be counted in the image. At 56, the ocular inflammation can be scored based on the number of inflammatory cells. The score can be on a continuous value scale, which can illustrate a degree of inflammation.

In some instances, the score can be stored in memory and later used as a reference value. Referring now to FIG. 5, illustrated is a method 60 for tracking the progress of an optical condition based on the reference value. At 62, a historical score can be retrieved. In some instances, the historical score can be retrieved from a non-transitory memory. In other instances, the historical score can be retrieved from a central cloud server or the internet. At 64, a current score for current ocular inflammation can be determined (e.g., according to method 40 of FIG. 3 or method 50 of FIG. 4). At 66, the historical score can be compared to the current score. A relative change in the inflammation and/or in the degree of inflammation can be output based on the comparison. Any relative change can be automatically detected and output. The scores can be stored in memory in a record of the ocular inflammation for the patient.

V. Example Computer System

Figure 6:
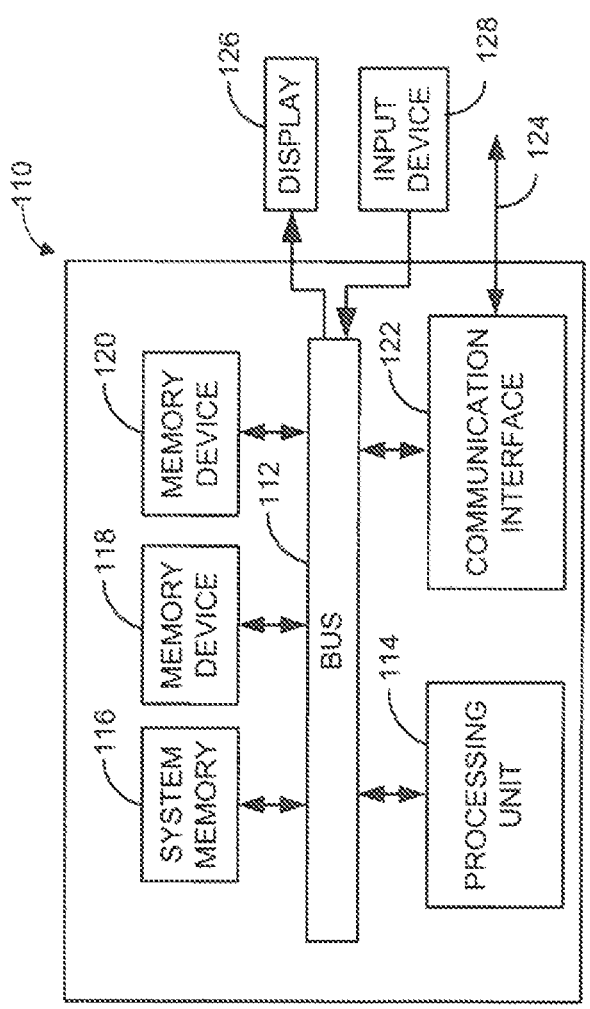
FIG. 6 is a schematic block diagram depicting an exemplary system of hardware components capable of implementing examples of the systems and methods depicted in FIGS. 1-5.

FIG. 6 is a schematic block diagram illustrating an exemplary system 110 of hardware components capable of implementing examples of the systems and methods of FIGS. 1-5. For example, the system 110 can represent the analysis device 12. The system 110 can include various systems and subsystems, including a personal computer, a laptop computer, a workstation, a computer system, an appliance, an application-specific integrated circuit (ASIC), a server, a server blade center, a server farm, etc.

The system 110 can includes a system bus 112, a processing unit 114, a system memory 116, memory devices 118 and 120, a communication interface 122 (e.g., a network interface), a communication link 124, a display 126 (e.g., a video screen), and an input device 128 (e.g., a keyboard and/or a mouse). The system bus 112 can be in communication with the processing unit 114 and the system memory 116. The additional memory devices 118 and 120, such as a hard disk drive, server, stand alone database, or other non-volatile memory, can also be in communication with the system bus 112. The system bus 112 interconnects the processing unit 114, the memory devices 116-120, the communication interface 122, the display 126, and the input device 128. In some examples, the system bus 112 also interconnects an additional port (not shown), such as a universal serial bus (USB) port. The processing unit 114 can be a computing device that executes a set of instructions to implement the operations of examples disclosed herein. The processing unit 114 can include a processing core.

The additional memory devices 116, 118 and 120 can store data, programs, instructions, database queries in text or compiled form, and any other information that can be needed to operate a computer. The memories 116, 118 and 120 can be implemented as tangible computer-readable media (integrated or removable) such as a memory card, disk drive, compact disk (CD), or server accessible over a network. In certain examples, the memories 116, 118 and 120 can comprise text, images, video, and/or audio, portions of which can be available in formats comprehensible to human beings. Additionally or alternatively, the system 110 can access an external data source or query source through the communication interface 122, which can communicate with the system bus 112 and the communication link 124.

In operation, the system 110 can be used to implement one or more parts of a system that can analyze ocular inflammation in accordance with the present invention. Computer executable logic for implementing the identification and development system resides on one or more of the system memory 116, and the memory devices 118, 120 in accordance with certain examples. The processing unit 114 executes one or more computer executable instructions originating from the system memory 116 and the memory devices 118 and 120. The term "computer readable medium" as used herein refers to a medium that participates in providing instructions to the processing unit 114 for execution, and can, in practice, refer to multiple, operatively connected apparatuses for storing machine executable instructions.

VI. Examples

The following example is for the purpose of illustration only is not intended to limit the scope of the appended claims.

This Example demonstrates the feasibility of utilizing spectral domain optical coherence tomography (SDOCT) in an automated manner to objectively image and grade the degree of anterior chamber inflammation.
Methods
Subjects This was an observational, prospective, consecutive case series of patients presenting to the Cleveland Clinic Cole Eye Institute uveitis clinic with active anterior segment uveitis between June 2012-June 2013. Patients were excluded if they had any corneal opacity preventing adequate imaging of the anterior chamber. Both eyes were included if there was a diagnosis of uveitis involving the anterior segment in both eyes. Written informed consent was obtained prior to undergoing ASOCT imaging. This study had prior approval from the Cleveland Clinic Institutional Review Board, complied with the Health Insurance Portability and Accountability Act of 1996 and followed the tenets of the Declaration of Helsinki. Clinicaltrials.gov identifier NCT01746537.
Clinical Examination A detailed slit-lamp examination was performed in all cases by a uveitis specialist (SKS or CYL). The degree of inflammation in the eye was graded utilizing the SUN grading system. In short the number of cells seen in a standard field defined by a 1 mm by 1 mm slit beam was counted. The ordinal scale was 0 for no detected cells, 0.5+ for 1-5 cells per field, 1+ for 6-15 cells, 2+ for 16-25 cells, 3+ for 26-50 cells and 4+ for greater than 51 cells. Any other ancillary testing was performed as deemed necessary for clinical diagnosis. The presence or absence of pigment or other changes was recorded. The clinical grade was recorded prior to performing optical coherence tomography (OCT) imaging and the grade was not changed based on the result of OCT imaging.
OCT Examination All patients were imaged on the RTVue-100® (Optuvue, Inc, Fremont, Calif.) by one investigator (KB). The RTVue-100/CAM is a spectral domain OCT device with a corneal adaptor module (CAM) used to image the cornea and anterior segment of the eye. It has a scanning speed of 26,000 A-scans/second, with an axial resolution in tissue of 5 µm. RTVvue-100/CAM includes two cornea lens adapters for imaging the cornea and anterior chamber of the eye. The low magnification corneal lens adaptor (CAM-L) was used for this study. This lens provides a scan length from 2-6 mm and a scan depth of 1.96 mm in tissue for corneal/anterior segment scanning.

All line scans were centered on the corneal apex with the posterior corneal boundary visible on all scans. Poor quality or misaligned scans were retaken without saving. All of the OCT scans contained the posterior corneal boundary, a highly reflective spike corresponding to the corneal apex and some scans contained portion of the iris and/or lens. High resolution line scans consisted of a 6 mm single B-scan at the central cornea. 3D Volume scans consisted of a 6 mm×6 mm cube consisting of 512 B-scans each with 128 A-scans. All OCT images were evaluated in grayscale. Volume scans were centered inferior to the corneal apex to avoid the superior lid margin and lashes.
Automated Algorithm An automated algorithm was developed to scan through all of the OCT scans comprising a 6 mm by 6 mm volume scan and counting the number of cells seen in the anterior chamber. The algorithm first determined the location of the cornea and the hyper-reflective stripe representing the central cornea and excluded these regions from the cell count. It then went through each scan and counted the number of hyper-reflective spots seen in the scan above a certain threshold reflectance value. The number of hyper-reflective spots was then tallied and output as a final cell count. The total volume measured was also calculated by the automated algorithm. The number of cells counted per $mm^3$ was then calculated.
Grading and Statistical Analysis The high resolution single line scans were evaluated by one of the investigators (SS) masked to clinical grade to determine the number of hyper-reflective spots seen in the scan. Each of the individual B-scans in the 3D volume scans was examined to count each hyper-reflective spot. The manual grading of number of hyper-reflective spots on the high resolution line scan and in the 3D volume scans were compared to clinical grading by Spearman correlation coefficients. The automated cell count determined by the algorithm for each of the 3D volume scans was compared to the manual cell count by Spearman correlation coefficients. Spearman correlation coefficients were chosen due to non-parametric data. All P-values reported are two-tailed and represent Gaussian approximations. All statistical analyses were performed with JMP Pro 11.1.1 (SAS Institute, Cary, N.C.).

Results

Clinical Demographics

A total of 83 eyes from 50 patients with anterior segment involving uveitis from a variety of diagnosis (Table 1) were included in the high resolution line scan portion of this study.

TABLE 1 diagnosis for each patient included in the study

| Diagnosis | Number of Eyes - High Resolution Line Scan | Number of Eyes - 3D Cube Scans |
|---|---|---|
| Idiopathic | 34 | 10 |
| HLA B27 | 17 | 7 |
| Juvenile Idiopathic Arthritis | 12 | 7 |
| Sarcoidosis | 10 | 4 |
| VKH | 6 | 1 |
| HSV | 2 | 0 |
| Behcets | 2 | 0 |
| Psoriatic Arthritis | 0 | 2 |

The average age of the patients was 43.3 (range 12-94). There were 34 females and 16 males. Of these 83 eyes, 24 eyes (28.9%) had grade 0 AC cells on slit lamp examination, 5 eyes (6.0%) had grade 0.5+ AC cells, 16 eyes (19.3%) had grade 1+ AC cells, 15 eyes (18.1%) had grade 2+ AC cells, 11 eyes (13.3%) had grade 3+ AC cells, 12 eyes (14.5%) had grade 4+ AC cells (Table 2).

TABLE 2 clinical grade compared to range and average for number of cells seen on individual line scan

| Clinical Exam Grade | Number of Eyes | Avg # of Cells on OCT Line Scan | Range of Cells on OCT Line Scan |
|---|---|---|---|
| 0 | 24 | 0.13 | 0-1 |
| 1/2+ | 5 | 1.2 | 0-3 |
| 1+ | 16 | 2.6 | 1-4 |
| 2+ | 15 | 5.7 | 3-8 |
| 3+ | 11 | 15.5 | 7-28 |
| 4+ | 12 | 41.2 | 23-75 |

Single Line OCT Results

Single line OCT results are shown in Table 2. There was an average of 0.13 cells for grade 0 AC cell (range 0-1), 1.2 cells (range 0-3) for grade 0.5+ AC cell, 2.6 cells (range 1-4) for grade 1+ AC cell, 5.7 cells (range 3-8) for grade 2+ AC cell, 15.5 cells (range 7-28) for grade 3+ AC cell, and 41.2 cells (range 23-75) for grade 4+ AC cell (Table 2). Comparing the manual grading of OCT line scans to the SUN clinical grade gave a Spearman correlation coefficient of r=0.967 (P<0.0001).

Three Dimensional Cube OCT Results

A total of 31 eyes from 26 patients with a variety of diagnosis (Table 1) were included to validate the automated algorithm. The patients used for the high resolution line scans were different from the patients used to validate the automated algorithm. The average age of the patients was 35.1 (range 8-68). There were 22 females and 8 males. Of these 31 eyes, 5 eyes (16.1%) had grade 0 AC cells on slit lamp examination, 6 eyes (19.4%) had grade 0.5+ AC cells, 6 eyes (19.4%) had grade 1+ AC cells, 4 eyes (12.9%) had grade 2+ AC cells, 5 eyes (16.1%) had grade 3+ AC cells, 5 eyes (16.1%) had grade 4+ AC cells.

Manual grading of three dimensional cube scans revealed an average of 9.2 cells for grade 0 AC cell (range 2-26), 10.0 cells (range 4-31) for grade 0.5+ AC cell, 16.3 cells (range 10-27) for grade 1+ AC cell, 31.5 cells (range 18-56) for grade 2+ AC cell, 138.6 cells (range 26-352) for grade 3+ AC cell, and 936.8 cells (range 12-2719) for grade 4+ AC cell (Table 3).

TABLE 3 clinical grade with corresponding automated and manual cell counts from 3D volume scans

| Cells on Clinical Exam | Average Number of Cells Automated | Average Number of Cells Manual | Average Cell Density/mm$^3$ |
|---|---|---|---|
| 0 | 13.6 | 9.2 | 0.268 |
| 1/2+ | 17.5 | 10.0 | 0.366 |
| 1+ | 23.5 | 16.33 | 0.463 |
| 2+ | 40.3 | 31.5 | 0.783 |
| 3+ | 121.6 | 138.6 | 2.372 |
| 4+ | 527.2 | 936.8 | 11.05 |

By automated grading there was an average of 13.6 cells for grade 0 AC cell (range 5-24), 17.5 cells (range 11-35) for grade 0.5+ AC cell, 23.5 cells (range 11-49) for grade 1+ AC cell, 40.3 cells (range 23-59) for grade 2+ AC cell, 121.6 cells (range 23-285) for grade 3+ AC cell, and 527.2 cells (range 17-1441) for grade 4+ AC cell (Table 3). The average cell density per mm$^3$ by the automated method was 0.268 for grade 0, 0.366 for grade 0.5+, 0.463 for grade 1+, 0.783 for grade 2+, 2.372 for 3+ and 11.05 for grade 4+.

The Spearman correlation coefficients were r=0.7765 (95% confidence interval 0.5993-0.8967, P<0.0001) and r=0.7484 (95% confidence interval 0.5500-0.8812, P<0.0001) comparing the manual and automated cell counts to the clinical grade, respectively. The Spearman correlation coefficient was 0.9043 (P<0.0001) and the pairwise correlation was 0.997 (95% confidence interval 0.9939-0.9986, P<0.0001) comparing the manual to the automated cell count.

From the above description, those skilled in the art will perceive improvements, changes and modifications. Such improvements, changes and modifications are within the skill of one in the art and are intended to be covered by the appended claims.

What is claimed is:

1. A system that analyzes ocular inflammation, comprising:
   a memory to store computer-executable instructions; and
   a processor that executes the computer-executable instructions to at least:
   receive an image of a portion of a patient's eye taken by a non-contact imaging modality, wherein the image comprises a three-dimensional volume of the portion of the patient's eye;

determine a diagnostic parameter for ocular inflammation from the image of the portion of the eye, wherein the diagnostic parameter is based on a number of identified inflammatory cells within the three-dimensional volume determined as at least one pixel having a greater than a background value of surrounding pixels;

score the ocular inflammation with a continuous value based on the diagnostic parameter; and output the score to a display device.

2. The system of claim 1, wherein the continuous value comprises a ratio of the number of inflammatory cells to a total volume of the three-dimensional volume scan of the portion of the eye.

3. The system of claim 1, wherein the at least one pixel comprises a reflectance value greater than at least two times a reflectance value of a background pixel.

4. The system of claim 1, wherein the score is determined based on comparing the diagnostic parameter to a second diagnostic parameter taken at an earlier time.

5. The system of claim 1, wherein the non-contact imaging modality comprises optical coherence tomography.

6. A method for analyzing ocular inflammation, comprising:

receiving, by a system comprising a processor, an optical coherence tomography image of a portion of a patient's eye, wherein the image comprises a three-dimensional volume of the portion of the patient's eye;

determining, by the system, a diagnostic parameter for ocular inflammation based on the image, wherein the diagnostic parameter is based on a number of identified inflammatory cells within the three-dimensional volume determined as at least one pixel having a greater than a background value of surrounding pixels;

scoring, by the system, the ocular inflammation with a continuous value based on the diagnostic parameter; and outputting, by the system, the score for the ocular inflammation to a display device.

7. The method of claim 6, wherein the scoring further comprises comparing the diagnostic parameter to a second diagnostic parameter taken at an earlier time.

8. The method of claim 6, wherein the optical coherence tomography image comprises a three-dimensional cube scan.

9. The method of claim 8, wherein the diagnostic parameter comprises at least one of a volumetric diagnostic parameter or an absolute diagnostic parameter.

10. The method of claim 6, wherein the continuous value correlates to a degree of inflammation.

11. The method of claim 6, wherein the ocular inflammation is at least one of inflammation of the sclera of the eye, inflammation of the posterior segment of the eye, or inflammation of the anterior chamber of the eye.

12. The method of claim 11, wherein the diagnostic parameter comprises at least one of a number of inflammatory cells, a thickness, a density, and an opacity.

13. A non-transitory computer-readable medium storing instructions executable by one or more processors to cause a computing device to perform operations, the operations comprising:

receiving an optical coherence tomography image of a portion a patient's eye, wherein the image comprises a three-dimensional volume of the portion of the patient's eye;

identifying inflammatory cells in the cross-section of the patient's eye based on the optical coherence tomography image;

counting the identified inflammatory cells;

scoring a degree of ocular inflammation for the patient based on the counting relative to a previously determined score for the patient;

detecting a change in the degree of ocular inflammation compared to a previous degree of ocular inflammation; and outputting the score to a display device, wherein the score is output with an indication of the change in the degree of ocular inflammation.

14. The non-transitory computer-readable medium of claim 13, wherein the operations further comprise storing the score in memory with a previously determined score to create a record of ocular inflammation for the patient creating a continuous measurement scale of ocular inflammation for the patient.

15. The non-transitory computer-readable medium of claim 13, wherein the scoring is based on at least one of an absolute number of counted inflammatory cells or a volume-based number of counted inflammatory cells.

16. The non-transitory computer-readable medium of claim 13, wherein the portion of the eye in the optical coherence tomography image comprises a three-dimensional volume of at least a portion of the eye.

* * * * *